United States Patent [19]

Chaumette et al.

[11] Patent Number: 4,791,141

[45] Date of Patent: Dec. 13, 1988

[54] PROCESS FOR SYNTHESIZING A MIXTURE OF PRIMARY ALCOHOLS FROM A SYNTHESIS GAS IN THE PRESENCE OF A CATALYST CONTAINING COPPER, COBALT, ZINC AND ALUMINUM

[75] Inventors: Patrick Chaumette, Bougival; Philippe Courty, Houilles; Daniel Durand, Rueil Malmaison; Pierre Grandvallet, Marly; Christine Travers, Rueil Malmaison, all of France

[73] Assignee: Institut Francais Du Petrole, Rueil-Malmaison, France

[21] Appl. No.: 928,655

[22] Filed: Nov. 5, 1986

Related U.S. Application Data

[63] Continuation of Ser. No. 732,488, May 10, 1985, abandoned.

[30] Foreign Application Priority Data

May 10, 1984 [FR] France ................. 84 07394

[51] Int. Cl.$^4$ ............... C07C 27/06; C07C 31/02
[52] U.S. Cl. ....................... 518/713; 518/700; 502/325
[58] Field of Search ................. 518/700, 713

[56] References Cited

U.S. PATENT DOCUMENTS

4,122,110 10/1978 Sugier et al. .
4,291,126 9/1981 Sugier et al. .
4,346,179 8/1982 Sugier et al. .
4,477,594 10/1984 Green et al. .

FOREIGN PATENT DOCUMENTS

2118061 10/1983 United Kingdom .

Primary Examiner—Howard T. Mars
Attorney, Agent, or Firm—Millen & White

[57] ABSTRACT

Process for manufacturing primary alcohols by reacting carbon oxides with hydrogen, in the presence of a catalyst containing, as essential elements, copper, zinc and aluminum, in respective atomic ratios of $Zn/Al=0.4:1$ to $2:1$ $Co/Al=0.2:1$ to $0.75:1$; $Cu/Al=0.1:1$ to $3:1$, the proportion by weight of each metal with respect to the total metals weight being: copper: 10–50%; cobalt: 5–25%; aluminum: 5–30%; zinc: 10–70%, the homogeneity of the catalyst being such that the variations of the atomic ratios Al/Co, Cu/Cc, Zn/Co within the catalyst, at the scale of 5 nanometers are lower than 15% with respect to the average value of said ratio. The catalyst may be prepared by complexing or by coprecipitation of the catalyst elements.

23 Claims, No Drawings

PROCESS FOR SYNTHESIZING A MIXTURE OF PRIMARY ALCOHOLS FROM A SYNTHESIS GAS IN THE PRESENCE OF A CATALYST CONTAINING COPPER, COBALT, ZINC AND ALUMINUM

This application is a continuation of application Ser. No. 732,488 filed May 10, 1985 now abandoned.

This invention relates to a catalytic process for manufacturing a mixture of methanol and higher alcohols by reaction of carbon oxides with hydrogen. The obtained alcohols are mainly saturated primary alcohols.

BACKGROUND OF THE INVENTION

U.S. Pat. Nos. 4,122,110 and 4,291,126 and French Pat. No. 2,523,957, disclose the use of catalysts in a process for manufacturing a mixture of alcohols from CO, $H_2$ or CO, $CO_2$, $H_2$ mixtures. These catalysts generally have a good selectivity in the conversion of carbon oxides and hydrogen to alcohols, and their selectivity to $C_2$ and higher saturated linear primary alcohols is often higher than 70% by weight. Furthermore, their initial productivity is substantial and very often at least about 0.1 ton of alcohols per ton of catalyst per hour.

The obtained alcohols have many uses; in particular the production of a high proportion of $C_2$–$C_6$ alcohols is interesting for the use in admixture with hydrocarbon cuts, as mixed hydrocarbons-alcohols motor fuels. As a matter of fact the higher alcohols are more compatible with hydrocarbons than methanol and, in addition, facilitate the incorporation of methanol thereto.

SUMMARY OF THE INVENTION

It has now been found that mixtures of particularly pure alcohols can be obtained by using catalysts of improved stability having particularly long life time. The catalysts, used according to the invention in the reaction of carbon oxides with hydrogen, contain at least copper, cobalt, aluminum and zinc; the atomic ratios between these metals are: Zn/Al=0.4:1–2:1, Co/Al=0.2:1)–0.75:1, Cu/Al=0.1:1–3:1, the amount of each metal element in proportion to the total weight of the metals being:

copper: 10–50%
cobalt: 5–25%
aluminum: 5–30%
zinc: 10–70% the proportion by weight of alkali and/or alkaline-earth metals being 0–0.095% and the variations of each of the atomic ratios within the catalyst, Al/Co, Cu/Co and Zn/Co, being lower than 15% with respect to the average value of said ratio at the scale of 5 nanometers.

When they contain a small proportion of alkali and/or alkaline-earth metals, the latter generally originate from the coprecipitation reactant used during the preparation and accordingly constitute impurities whose content will be reduced by washing, if necessary, to less than 0.095% by weight in proportion to the total metals weight. The content of alkali and/or alkaline-earth metals will preferably range from 0 to 0.05% by weight. The atomic ratio of alkali and/or alkaline-earth metals to Al is advantageously from 0:1 to 0.02:1, preferably from 0:1 to 0.009:1 and more preferably from 0:1 to 0.003:1.

The catalysts according to this invention differ from those of the prior art by the following points, considered separately or in combination:

the produced mixture of alcohols, which contains 10–50% by weight of homolog higher alcohols in proportion to the total weight of alcohols, usually does not contain more than 1% of organic impurities (esters, liquid hydrocarbons, ketones and aldehydes) in proportion of the total weight of organic compounds.

when contacted with the synthesis gas, the exothermic effects are considerably lower than those of the prior art catalysts which, in addition to the above-mentioned metals, further contain at least one alkali metal. For these alkalinized catalysts, the thermal effects seem to result from a transitory methanation reaction, highly exothermic, which operates with a progressive substitution of the inert gas contained in the unit (after reduction with hydrogen and before admission of the synthesis gas) with said synthesis gas. The new catalysts of the invention result in a considerably reduced transitory methanation giving them a decisive advantage as concerns the industrial use and the security of operation.

In this application the term "synthesis gas" means a gas containing carbon monoxide, carbon dioxide and hydrogen. In the catalysts of the invention, zinc may be at least partly substituted with one or more metals B, selected from the group consisting of cadmium and manganese (in manganous state $Mn^{2+}$) and aluminum may optionally be substituted, at least partly, with one or more metals C, selected from the group consisting of chromium, manganese (in manganic state $Mn^{3+}$) and titanium.

These catalysts may also furthercontain about 0.01–1% by weight and preferably about 0.02–0.8% by weight, in proportion to the total metals weight, of one or more additional metals M selected from the noble metals from group VIII (ruthenium, rhodium, palladium, osmium, iridium and platinum) and preferably one or more additional metals M selected from the group consisting of rhodium, palladium and platinum.

The respective proportions of these different metals (in % by weight with respect to the total metals weight) are as follows:

Copper: 10–50%, preferably 15–45%
Cobalt: 5–25%, preferably 9–20%
Aluminum: 5–30%, preferably 7–25%
Zinc: 10–70%, preferably 15–50%

Moreover, within the above-mentioned composition ranges, the different metals must be in the following relative atomic proportions to each other:

Zinc/Aluminum: 0.401–2:1, preferably 0.50:1–1.5:1
Cobalt/Aluminum: 0.2:1–0.75:1, preferably 0.25:1–0.55:1
Copper/Aluminum: 0.1:1–3:1, preferably 0.4:1–2:1

It is possible to substitute up to 50% of the zinc gram-atoms with at least one of the above-mentioned metals B; similarly, it is also possible to substitute up to 50% of the aluminum gram-atoms with at least one of the above-mentioned metals C. At least one metal B and at least one metal C may optionally be simultaneously present in the catalyst.

When zinc and/or aluminum is (are) at least partly substituted with at least one of the above-mentioned metals B and/or C, it is compulsory that the atomic ratio Zn/Al be from 0.40:1 to 2:1, preferably from 0.5:1 to 1.5:1.

The content of alkali and/or alkaline-earth metals of the final catalyst, expressed as the weight of alkali and/or alkaline-earth metals in proportion to the total metals weight, will range from 0 to about 0.095%, preferably from 0 to about 0.05% by weight.

The catalysts according to this invention, in order to be both active and stable in the synthesis of higher alcohols, and selective in the conversion of CO and $CO_2$ to oxygenated compounds (hydrocarbons are the by-products whose formation must be reduced to the greater extent), must be of very homogeneous composition and the more active metals thereof must be uniformly distributed within each elementary catalyst particle.

The best results, in terms of selectivity of CO and $CO_2$ conversion to oxygenated products and particularly to higher alcohols, are obtained with catalysts wherein the variation of the atomic ratio aluminum/cobalt is lower than 15% with respect to the average value of said ratio, and preferably lower than 10%, at the scale of 50 Å (5 nanometers).

The homogeneity of the composition at the scale of the nanometer may be controlled for example by X-ray spectrometry in a scanning transmission electron microscope (STEM) equipped with an X-rays detector of the doped silicon type covering the required space zone (for example 1–20 keV for the compositions according to the invention). The operation is as follows: a representative sample of catalyst is crushed to a fine powder (e.g. of a particle size smaller than 10 $\mu$m), then deposited on a grid of electron microscope, optionally after suspension in an organic solvent followed with the evaporation of the latter. The material of which the grid of electron microscope is made must be so selected as to avoid casual problems of spectral interferences or parasitic signals (for this reason copper grids cannot be used).

Satisfactory materials are: nylon, beryllium, carbon. The microscope must give images of high resolution (0.1 to 1 nm) in the scanning mode and also have a high sensitivity in the X-ray micro-analysis mode. The STEM Vacuum Generators HB 501 is an apparatus of the trade perfectly convenient (limit sensitivity better than 1000 atoms of a given element) for determining the catalyst homogeneity scale.

After selection of the zone to be analyzed (typically 2–5 nm) several countings, during 100–1000 s, are made simultaneously, giving a counting statistic of sufficient accuracy (better than 10%).

From intensities measured on the various peaks selected for the various elements contained in the sample, their relative concentrations and their respective atomic ratios can be determined from well known X-ray techniques (see for example REED S. J. B.—Electron microprobe analysis, Cambridge University Press, 1975) for each particle of the sample.

The compared samples must have the same thickness. The average values of the correction coefficients are as follows:

Correction coefficients (on the basis of Co—$K_\alpha$=1).

| Measurement on the line | Element | Coefficient |
| --- | --- | --- |
| $K_\alpha$ | cobalt | 1.00 |
| $K_\alpha$ | copper | 1.10 |
| $K_\alpha$ | aluminum | 5.35 |
| $K_\alpha$ | zinc | 5.15 |

These coefficients have been determined by the applicant from mixed oxides roasted at high temperature ($CoAl_2O_4$, $CuAl_2O_4$, $ZnAl_2O_4$, $Cu_{0.5}Zn_{0.5}Al_2O_4$, $Co_{0.5}Zn_{0.5}Al_2O_4$ $Co_{0.5}Cu_{0.5}Al_2O_4$) forming the reference samples.

The Al/Co atomic ratio will be, for example, calculated by the formula:

$$Al/Co = 5.35\, i_{K_\alpha}Al / i_{K_\alpha}Co$$

Wherein $i_{K_\alpha}Al$ and $i_{K_\alpha}Co$ are the average raw intensities over several countings.

In order to obtain homogeneous catalysts, it is essential to first prepare a solution (homogeneous per se) containing copper, cobalt, aluminum, zinc and optionally at least one metal B and/or optionally at least one metal C and/or optionally a metal M, then to convert said solution, by complexation or by coprecipitation reaction, to a solid substance called catalyst precursor and having always a very homogeneous composition.

Cu, Co, Al, Zn and optionally B and/or C and/or M metals are used as soluble compounds, preferably soluble in acid medium, although the amminated complexes (soluble in ammonia medium) of copper, cobalt, zinc and some of the B and C metals may be used in addition to the alkaline and/or ammoniacal coprecipitation reactant.

By way of example the soluble oxides (e.g. ZnO), the hydroxides, carbonates, hydroxycarbonates soluble in acid medium (e.g. $CuCO_3$—$Cu(OH)_2$, $Co(OH)_2$), the nitrates, oxalates, tartrates, citrates, acetyl-acetonates or anionic combinations such as aluminate, chromate, bichromate, permanganate, oxalatocobaltate can be used. As soluble salts, nitrates are mostly used.

For preparing these catalysts, it is essential to use preparation technique leading to a product whose composition is as homogeneous as possible and avoiding the segregation of the different elements during the various unitary steps of preparation.

Preferred methods for preparing homogeneous catalyst masses giving homogeneous catalysts both active and selective in the production of higher alcohols and resulting in a minimum formation of hydrocarbons are described hereinafter. By these methods the desired homogeneity is maintained during the preparation steps.

A preferred method of preparation, already disclosed, as early as 1968, by the applicant in French Pat. Nos. 1,604,707 and 2,045,612 consists of preparing a solution containing Cu, Co, Al, Zn metals, optionally with B and/or C and/or M metals and of adding thereto at least one compound adapted to the formation of complexes selected preferably from:
  organic polyacids containing one or more acid groups, e.g. oxalic, malonic, succinic or glutaric acids.
  acid-alcohols, e.g. glycolic, lactic, malic, tartaric or preferably citric acids,
  amino-acids, e.g. aminoacetic acid, alanine or leucine,
  aminoalcohols as, for example monoethanolamine, diethanolamine, triethanolamine, in a proportion of about 0.5–2 gram-equivalent of $COO^-$ or $-NH_2$ per gram-equivalent of metals, $M^{n+}/n$.

The obtained solution is evaporated under vacuum (e.g. in a rotary evaporator) so as to obtain a solution having a viscosity of at least 1 Pa.S, which is transferred to a vacuum drier at a temperature of about 60° to about 120° C. and dried to a water content of less than 10% by weight. There is so obtained a transparent vitreous mass, homogeneous and amorphous in X-ray diffraction, which is then thermally activated in nitrogen or in the presence of an oxygen—containing gas, at a temperature ranging, for example from about 300° C. to about 600° C. for a sufficient time to reduce the content of volatile matters to less than 10% and preferably less than 6% by weight.

Another preferred preparation method consists of preparing, by means of at least one coprecipitation reaction, a homogeneous hydrated precursor containing Cu, Co, Al, Zn and optionally B and/or C and/or M. The coprecipitation reaction comprises admixing, under hereinafter defined operating conditions, a solution of soluble salts of Cu, Co, Al, Zn and optionally B and/or C and/or M metals with a solution of sodium and/or potassium and/or ammonium carbonate and/or hydrogenocarbonate and/or hydroxide, so as to obtain a coprecipitate which, after subsequent washing, forms the homogeneous hydrated precursor.

All the techniques and apparatuses of the prior art may be used or applied to perform the present invention; for example the solution of salts of Cu, Co, Al, Zn and other metals may be added to the alkaline solution or inversely. Preferably both solutions will be simultaneously added, their flow rates being regulated by the pH measured in the reaction zone, in a reactor equipped with an efficient stirring system. Preferably both solutions will be contacted in a zone of maximum turbulence defined by the volume surrounding the stirring apparatus, inside the reaction volume.

The average residence time, expressed in minutes and defined as the ratio of the total volume flow rate (liters/minute) of the solutions introduced into the reactor to the reactor volume, expressed in liters, may vary from 0.1 to 600 minutes, since the reaction may be conducted either in a continuously operating reactor (called stationary concentration reactor) or in a batchwise operating reactor. In the continuously operation reactor, whose useful volume ranges from a few $cm^3$ to about 10 liters, and where the residence time ranges from 0.1 to 15 minutes, the reaction product is recovered continuously (optionally after maturation in another reactor) and then fed, for example, to a press-filter or to a rotary filter where it is washed. In the batchwise operation the residence time is at least 30 minutes and preferably at least 60 minutes. The reactants are introduced continuously without simultaneously recovering the reaction product so that the reaction product remains in presence of the continuously introduced reactants. In this type of reactor whose volume (in accordance with the specifications of concentration of the considered solutions and of the catalyst amounts to be prepared) varies from 1 liter to about 1000 liters or more, the operation is conducted at variable concentrations, the other operating conditions remaining unchanged during the precipitation itself.

Another preferred embodiment of the invention consists of reacting, at a temperature of at least 50 and preferably at least 60° C., a solution of soluble salts of Cu, Co, Al, Zn and optionally B and/or C and/or M metals, at a total concentration of metals of at least 1 gram-atom per liter, for example from 0.1 to 1 g. at of metals per liter, with a solution of sodium and/or potassium and/or ammonium carbonate and/or hydrogenocarbonate and/or hydroxide at a maximum concentration of 2 g. at (e.g. from 0.1 to 2 g. at) of alkali metals and/or $NH^{4+}$ per liter, the coprecipitation reaction being conducted at a pH of $7\pm 1$ pH unit, and the residence time in the reaction medium ranging from 3 to 180 minutes, preferentially from 5 to 50 minutes. The obtained hydrated mixed hydroxycarbonate is homogeneous, at least partly crystallized in a rhombohedral structure.

This structure, which has already been observed in other compositions, e.g the pyroaurite, which is a hydrated iron and magnesium hydroxycarbonate (American Society for testing materials ASTM. Index card No. 25-521) may be indexed in a multiple hexagonal mesh with average parameters a=0.30-0.31 nm, c=2.24-2.25 nm and a hexagonal space group R-3M. The parameters may vary slightly in relation with the composition of said hydrated mixed hydroxycarbonate.

By way of example the X-ray diffraction diagram indexation of the hydrated crystallized precursor of catalyst A is given in table I.

TABLE I

Rhombohedral phase of hydroxycarbonate type hexagonal mesh a = 0.305 nm, c = 2.24 nm
Space group R - 3M

| Miller Index | d (nm) | $i/i_o$ |
|---|---|---|
| 003 | 0.749 | 100 |
| 006 | 0.373 | 35 |
| 012 | 0.258 | 20 |
| 104 | 0.240 | 4 |
| 015 | 0.228 | 12 |
| 107 | 0.204 | 2 |
| 018 | 0.192 | 9 |
| 1010 | 0.171 | 4 |
| 0111 | 0.1611 | 2 |
| 110 | 0.1530 | 4 |
| 113 | 0.1500 | 4 |
| 1013 | 0.1443 | 2 |
| 116 | 0.1415 | 2 |

Recording conditions: Cu $K_\alpha$ 35 KV 35 mA
Rear monochromator (graphite)

The crystallized compound may then be matured for example at 50°-100° C. under atmospheric pressure or at 100°-250° C. in an autoclave operated underpressure, for a period of 15 minutes to 5 hours, in the presence of its mother liquors or its washing waters. During this maturation step a pH increase, generally of at most 1.5 pH unit above the precipitation pH, may be observed. Unexpectedly this maturation treatment improves the crystallinity and/or increases the crystallites size of the crystallized hydrated precursor.

The maturation step, when the precipitation is conducted in batch, may be performed in the same reactor, after having stopped the reactants supply. It is also possible, when the precipitation is continuous, to recover the formed precipitate under stationary conditions (temperature, concentrations, pH, feeding rate of the reactants) and to mature it, after optional washing, in another reactor or in an autoclave.

Preferably, for the preparation of crystallized mixed hydroxycarbonate, the reaction temperature will be at least 70° C., the concentration of salts of Cu, Co, Al, Zn, (B), (C) and (M) metals in the solution will range from 0.1 to 0.6 g. at of metals per liter and the concentration of alkali metals and/or ammonium from 0.2 to 1.2 g. at per liter, the reaction time being from 5 to 50 minutes.

After precipitation and optional maturation in the mother liquors, the crystallized precipitate is washed so as to reduce its alkali content (expressed as the alkali weight in proportion to the total metals weight) to less than about 0.095% by weight and preferably to less than about 0.05%, and then optionally matured in the washing waters.

After precipitation and washing, a crystallized homogeneous hydrated precursor is obtained whose oxides content is about from 15 to 60% by weight.

In this crystallized precursor, the metals are distributed very homogeneously and the atomic ratios Cu/Co, Al/Co and Zn/Co and also optionally B/Co and/or C/Co and/pr M/Co, measured as above indicated, vary by less than 15% (relative variation) and preferentially by less than 10% at the scale of 5 nm (nanometers).

Drying of the crystallized hydrated precipitate may be performed in any known manner; for example in a stove at a temperature ranging for example from about 20° to about 150° C., so as to reduce its oxides content to about 65–85% by weight.

It is also possible to proceed by instantaneous drying, e.g by spray-drying, for example at 150°–350° C. for less than 10 seconds. The obtained product then consists of cenospheres of 3–700 μm diameter and of homogeneous composition. Such an instantaneous drying may alsio be achieved by combination of a drying in thin layer and a strong stirring. Such a device (e.g of the rotary type) gives small plates of dried catalyst of homogeneous composition containing Cu, Co, Al, Zn and optionally B and/or C and/or M metals in the above-mentioned proportions.

The precipitate is then thermally activated as follows:

The dried precipitate is treated at a temperature from about 250° to about 750° C., preferably in the range of about 300°–600° C., for a sufficient time, for example at least 0.5 hour, so as to obtain an activated homogeneous catalyst containing no more than 12% by weight of volatile matters (the proportion of volatile matters is measured for example by activation, in the presence of air, of a given weight of product, placed in a boat and roasted at 500°–600° C. for 4 hours).

The thermal activation may be conducted, for example, in the presence of an inert gas containing 0 to 50% of oxygen. A mixed homogeneous oxide is thus obtained wherein the Cu/Co, Al/Co and Zn/Co atomic ratios do not vary by more than 10% at the scale of 5 nm.

The thermal activation may also be performed in reducing medium (inert gas—reducing gas mixtures containing 0.1 to 100% of reducing gas); the reducing gases, used alone or as mixtures, being hydrogen or ammonia.

The thermal activation in a medium acting as a reducer, as a whole, may be performed either on the dried precursor or on the mixed oxide previously activated in oxidizing medium, as a whole.

After thermal activation in a medium acting as reducer, as a whole, the mixed oxide may be partially reduced (by the hydrogen-containing gas) or partially reduced and nitrided (by the ammonia-containing gas). It remains homogeneous after optional reduction and the reduction conditions must be so adjusted that the Cu/Co, Al/Co and Zn/Co atomic ratios do not vary by more than 10% at the scale of 5 nm.

A process combining the drying and thermal activation consists of preparing an aqueous suspension of wet crystallized precipitate, thoroughly dealkalinized, containing about 10–40% by weight of oxide, and of performing a flash-roasting in a spray-drier in the presence of a combustion gas containing less than 1 mg of sulfur per $N.M^3$ and having an inlet temperature of at least 500° C. Thus, microspheres of 10–700 μm are obtained, which can be used in a liquid process with catalyst circulation.

The thermally activated catalyst, particularly when activated in the presence of an inert gas containing 0–50% of oxygen, consists of a homogeneous mixed oxide phase, at least partly crystallized in a structure of spinel type, having a cubic elementary mesh whose parameter varies from about 7 to about 9.2 Angström (Å).

The homogeneous crystallized hydrated precipitate, thoroughly dealkalinized by washing, dried so as to reduce its content of volatile matters to less than 35% by weight, thermally activated at a temperature of 250°–600° C. for at least 0.5 hour, then optionally crushed, may then be optionally contacted with an aqueous or organic solution of at least one metal M selected from the group formed of palladium, platinum and rhodium, so as to uniformly disperse said metal and to obtain, after drying and thermal activation, a catalyst wherein said metal is well dispersed (the dispersion may be measured by chimisorption of reactant gases CO, $H_2$, on said metal, after selective reduction). With the exception of the halides and sulfates, all the soluble salts, for example the nitrates, acetylacetonates, as well as complexes, for example nitrosoamminated, amminated or carbonylated complexes, can be used. After impregnation, the catalyst will be dried and optionally thermally reactivated as above set forth.

Metal M may be introduced in another way by contacting the abovementioned aqueous or organic solution with the moist hydrated precursor, before drying, or with the dried hydrated precursor, before thermal activation. Metal M may also be introduced during the coprecipitation of the other metals (Cu, Co, Al, Zn, B and/or C).

If not already shaped, the catalyst, thermally activated in the above-mentioned conditions, will be shaped as follows:

The thermally activated, homogeneous product is crushed, for example to particles of less than 0.5 mm, admixed in a proportion of 0.5–5% of its weight with at least one pelletizing adjuvant selected from the group formed of graphite, stearic acid, stearates and optionally a porosity adjuvant selected from cellulose or cellulose-containing powders of vegetable origin, ammonium nitrate and carbonates, combustible textile fibers and naphthalene. Finally the product is pelletized to solid cylinders of 3–6 mm diameter or toric cylinders of 3–6 mm external diameter and 1–4 mm internal diameter and of 2–6 mm height.

The catalyst shaped to pellets will be optionally subjected to a final thermal activation in the above-mentioned operating conditions.

The thermally activated catalyst ready for use consists of a very homogeneous association of oxides (optionally some of them may be reduced, at least partly, when a thermal activation has been performed in a medium acting as reducer, as a whole). In this very homogeneous association of oxides, the metals, particularly copper, cobalt, aluminum and zinc are distributed very homogeneously, at the scale of 5 nm and the relative variations of the Cu/Co, Al/Co and Zn/Co atomic ratios are lower than 15% and preferably lower than 10%. The specific surface of said catalysts varies from about 20 to about 300 $m^2g^{-1}$.

The conditions of use of said catalysts for manufacturing alcohols are usually as follows: the catalyst charge, in the reactor, is first prereduced by a mixture of inert gas (e.g. nitrogen) with at least one reducing compound selected from the group consisting of hydrogen, carbon monoxide, alcohols and $C_1$ and $C_2$ aldehydes, the molar ratio "reducing compound/reducing compound+inert gas" being from 0.001:1 to 1:1.

The prereduction temperature generally varies from about 100° to 750° C. but preferably from about 150° to 550° C., the total pressure is usually about 0.1–10 MPa and preferably about 0.1–6 MPa; The hourly volume velocity is usually from $10^2$ to $4.10^4$ hour$^{-1}$ and preferably from $5.10^2$ to $10^4$ hour$^{-1}$.

After a first reduction phase conducted, for example, at about 150°–250° C. in the presence of the above mentioned reducing mixture and with a molar ratio "reducing gas/reducing gas+inert gas" ranging from 0.001:1 to 0.1:1 and preferably from about 0.005:1 to 0.05:1 for a sufficient time to obtain the same concentrations of reducing gas at the inlet and at the outlet of the reactor (thus making obvious that the first reduction step is completed), it may be advantageous, in a second step, to increase the temperature and, optionally, the concentration of reducing gas, and to continue the reduction under more severe conditions:

The reduction temperature then varies between about 220° and about 750° C. and preferably in the range of 240°–550° C., the molar ratio "reducing gas/reducing gas+inert gas" is then 0.01:1–1:1 and preferably 0.05:1–1:1, the pressure and hourly volume velocity remaining within the above-mentioned ranges.

The alcohols synthesis reaction itself is conducted in the following operating conditions: the pressure is usually about 2–25 MPa, preferably about 5–15 MPa, the molar ratio "$H_2/2 CO+3CO_2$" is advantageously about 0.4:1–10:1, but preferably 0.5:1–4:1, and the temperature ranges from about 200° to 400° C., and preferably from about 240° to 350° C.

The hourly volume velocity (expressed in volume NTP of gas mixture per volume of catalyst and per hour) is usually from about 1,500 to 60,000 h$^{-1}$ and preferably from 2,000 to 20,000 h$^{-1}$.

The catalyst may be used as fine calibrated powder (10–700 μm) or as particles of 2–10 mm equivalent diameter, in the presence of a gas phase or of a mixture of a liquid phase with a gas phase. The liquid phase may consist of one or more alcohols and/or hydrocarbons having at least 5 and preferably at least 10 carbon atoms.

In this embodiment, it is preferable taht the surface velocities of the gas and the liquid, under the temperature and pressure conditions of the process, be at least about 1.5 cm/sec. and preferably at least about 3 cm/sec. By surface velocity, it is meant the ratio of the flow rate by volume to the cross-sectional area of the reactor, considered empty of catalyst.

The catalysts having the above-described compositions are particularly active and stable in the reaction of $C_1$–$C_6$ primary alcohols synthesis from a gas containing carbon monoxide and hydrogen or from a synthesis gas. They lead to the production of mixtures of highly pure alcohols.

These catalysts may also be used in other reactions involving carbon oxides, particularly in the conversion of carbon dioxide by water (shift conversion).

EXAMPLES

The invention will be further illustrated in a non limitative manner by the following examples concerning various aspects of one of the applications of the catalysts: the synthesis of $C_1$–$C_6$ alcohols from synthesis gas.

EXAMPLE 1 (CATALYST A)

144.96 g of trihydrated cupric nitrate (0.6 g at Cu), 116.41 g of hexahydrated cobalt nitrate (0.4 g. at Co), 450.15 g of nonahydrated aluminum nitrate (1.2 g. at Al), 267.72 g of hexahydrated zinc nitrate (0.9 g.at Zn) are dissolved into 6 liters of bi-exchanged water so as to obtain a solution (solution I) containing 0.52 g.at of metals per liter.

Separately, 427.18 g of disodic carbonate are dissolved into 7 liters of bi-exchanged water. The resultant solution II contains 1.15 g.at of sodium per liter.

The reaction is conducted in a reactor of 1100 ml operated continuously. Both solutions I and II are simultaneously introduced into the reactor already containing 1 liter of water at a temperature of 60°–70° C. The temperature is maintained within the range of 60°–70° C. during the whole precipitation period. The residence time is about 12 mm.

The flow rates are regulated by the pH which varies between 6.8 and 7.2 during the whole reaction period. The reaction product is recovered continuously in another reactor, matured ½ hour in the mother liquors at 80° C., filtered and washed with three times 12 liters of bi-exchanged water. The resultant product then contains 25% by weight of potential oxides in proportion to its total weight. The precipitate is then dried in a ventilated stove with open circuit at 90° C. for 16 hours, then at 120° C. for 3 hours. The obtained dry product then contains 80% by weight of potential oxides in proportion to its total weight. It is crystallized, its X-ray diffraction diagram has been indexed and the results are given in table I above. The so-obtained precipitate contains 0.035% by weight of sodium in proportion to the sum of metals.

The microscopic survey shows a good homogenity of the product. The Cu/Co, Al/Co and Zn/Co vary in the respective ranges of 1.35–1.65, 2.8–3.2 and 2.05–2.4. The maximum variation of each of these ratios is of about 10% of its average value at the scale of 5 nanometers. The product is then thermally activated for 3 hours at 450° C. in air; its content of volatile matter is then about 10% by weight; it consists of a crystallized mixed oxide phase, partly in spinel structure whose elementary mesh parameter is 8.15 Å.

This product is then pelletized to solid cylinders of 4 mm diameter, after addition of 2% by weight of graphite. Before being charged in the unit, catalyst A is subjected to a final thermal activation for 2 hours at 350° C.; the content of volatile matters is then 3% by weight with respect to the catalyst weight.

EXAMPLE 2 (CATALYST B)

Catalyst B differs from catalyst A in that the Zn/Al ratio is that of a stoichiometrical zinc aluminate. 217.44 g of trihydrated cupric nitrate (0.9 g.at Cu), 116.41 g of hexahydrated cobalt nitrate (0.4 g.at Co), 450.15 g of nonahydrated aluminum nitrate (1.2 g.at Al) and 178.48 g of hexahydrated zinc nitrate (0.6 g.at Zn) are dissolved in 6 liters of bi-exchanged water, thus giving a solution (solution I) containing 0.52 g.at of metals per liter.

Separately 427.18 g of disodic carbonate are dissolved into 7 liters of bi-exchanged water. A solution II is obtained, which contains 1.15 g.at of sodium per liter.

Precipitation, thermal activation and shaping are the same as in example 1. The product obtained by precipitation is homogeneous at the scale of 5 nanometers; the variation of Cu/Co, Al/Co and Zn/Co ratios is lower than 15% with respect to the average value of each of them.

EXAMPLE 3 (CATALYST C)

This example is given by way of comparison.

Catalyst C differs from catalysts A and B, as described in the preceding examples, in that its Zn/Al ratio is that of a zinc aluminate of sub-stoichiometrical zinc amount.

253.69 g of trihydrated cupric nitrate (1.05 g.at Cu), 116.41 g of hexahydrated cobalt nitrate (0.4 g.at Co), 450.15 g of nonahydrated aluminum nitrate (1.2 g.at Al) and 133.86 g of hexahydrated zinc nitrate (0.45 g.at Zn) are dissolved into 6 liters of bi-exchanged water so as to obtain a solution (solution I) containing 0.52 g.at of metals per liter.

Separately 427.18 g disodic carbonate are dissolved into 7 liters of bi-exchanged water. A solution II, containing 1.15 g.at of sodium per liter, is obtained.

Precipitation, thermal activation and shaping are the same as in example 1.

EXAMPLE 4 (CATALYST D)

This example is given by way of comparison.

Catalyst D differs from catalyst A in that the roasting step is followed with an alkalinization step.

150 g of oxides, crushed to a powder of particle size of at most 0.2 mm, are contacted with a solution containing 6.14 g of disodic carbonate in 230 cc of bi-exchanged water and then mixed for 30 minutes. The resultant paste is dried in thin layer for 6 hours at 70° C. with covered plate and then 16 hours at 90° C. with uncovered plate in a ventilated stove. The thermal treatments and the pelletizing step are the same as in example 1.

The so-obtained catalyst contains 1.72% by weight of sodium in proportion to the total metals weight.

EXAMPLE 5 (CATALYST E)

This example is given by way of comparison.

Catalyst E differs from catalyst D in that it contains 5.17% by weight of sodium in proportion to the total metals weight.

150 g of oxide, crushed to a powder of particle size at most equal to 0.2 mm, are contacted with a solution containing 19.66 g of disodic carbonate in 230 cc of bi-exchanged water and then mixed for 30 minutes.

The drying step is the same as for catalyst D. The thermal treatments and the pelletizing step are the same as in example 1.

EXAMPLE 6 (CATALYST F)

Catalyst F differs from catalyst A only in that the precipitate obtained after coprecipitation is washed with five times 12 liters of bi-exchanged water instead of 3 times 12 liters. The sodium content by weight in proportion to the total metals, is then close to 0.01% (100 ppm). The other preparation steps are the same as in example 1.

EXAMPLE 7 (CATALYST G)

450.15 g of nonahydrated aluminum nitrate (1.2 g.at Al), 267.2 g of hexahydrated zinc nitrate (0.9 g.at Zn) and 345.82 g of citric acid (1.8 moles) are dissolved in 2 liters of water heated to 80° C. Then 69 g of copper basic carbonate of 55.3% copper content, i.e. 0.6 g.at Cu and 42.8 g of cobalt carbonate (2CoCO$_3$, 3CoO, 4H$_2$O) of 55.10% cobalt content, i.e. 0.4 g.at Co, are slowly added and heating is maintained until complete dissolution of these products.

The solution is then evaporated in a rotary evaporator up to a viscosity of 1.5 Pa, then dried in a vacuum drier at 80° C. for 24 hours. The obtained homogeneous vitrous mass is roasted at 400° C., in a rotary furnace, at a rate of 100 g/h. The residence time is 3 hours. The pelletizing and roasting steps are the same as in example 1.

EXAMPLE 8 (CATALYST H)

Catalyst H differs from catalyst A in that, during its preparation, 0.2 mole of aluminum nitrate is replaced with 0.2 mole of manganese nitrate and in that the pH of the precipitation has been regulated at 7.2±0.1 pH unit.

144.96 g of trihydrated cupric nitrate (0.6 g.at Cu), 116.41 g of hexahydrated cobalt nitrate (0.4 g.at Co), 375.13 g of nonahydrated aluminum nitrate (1.0 g.at Al), 267.72 g of hexahydrated zinc nitrate (0.9 g.at Zn) and 57.41 g of hexahydrated manganese nitrate (0.2 g.at Mn) are dissolved in 6 liters of bi-exchanged water so as to obtain a solution (solution I) containing 0.52 g.at of metals per liter.

Separately 427.18 g of disodic carbonate are dissolved in 7 liters of bi-exchanged water. Solution II, containing 1.15 g.at of sodium per liter, is thus obtained.

Precipitation, thermal activation and shaping are the same as in example 1. The product obtained by precipitation was found homogeneous at the scale of 5 nanometers: the variation of Cu/Co, Al/Co, Zn/Co and Mn/Co ratios is lower than 15% with respect to the average value of each of them.

EXAMPLE 9 (CATALYST I)

Catalyst I differs from catalyst A by the replacement, during the preparation, of 0.1 mole of zinc nitrate with 0.1 mole of cadmium nitrate and by the regulation of the precipitation pH at 7.2±0.1 pH unit.

144.96 g of trihydrated cupric nitrate (0.6 g.at Cu), 116.41 g of hexahydrated cobalt nitrate (0.4 g.at Co), 450.15 g of nonahydrated aluminum nitrate (1.2 g.at Al), 237.97 g of hexahydrated zinc nitrate (0.8 g.at Zn) and 30.85 g of tetrahydrated cadmium nitrate (0.1 g.at Cd) are dissolved in 6 liters of bi-exchanged water, thus giving solution I containing 0.52 g.at of metals per liter.

Separately 427.18 g of disodic carbonate are dissolved in 7 liters of bi-exchanged water. A solution II is thus obtained, which contains 1.15 g.at of sodium per liter.

Precipitation, thermal activation and shaping are the same as in example 1. The product obtained by precipitation was found homogeneous at the scale of 5 nanometers: the variation of Cu/Co, Al/Co, Zn/Co and Cd/Co ratios is lower than 15% with respect to the average value of each of them.

EXAMPLE 10 (Catalyst K)

Catalyst K contains the same metals as catalyst A but in different proportions (see Table II).

157.04 g of trihydrated cupric nitrate (0.65 g.at Cu), 115.41 g of hexahydrated cobalt nitrate (0.4 g.at Co), 337.62 g of nonahydrated aluminum nitrate (0.9 g.at Al) and 297.47 g of hexahydrated zinc nitrate (1.0 g.at Zn) are dissolved in 6 liters of bi-exchanged water so as to obtain a solution I containing 0.49 g.at of metals per liter.

Separately 460.51 g of disodic carbonate are dissolved in 7 liters of bi-exchanged water, giving a solution II containing 1.10 g.at of sodium per liter.

Preparation, thermal activation and shaping are the same as in example 1.

EXAMPLE 11 (CATALYST M)

Catalyst M differs from catalyst A in that solution I further contains palladium nitrate in addition to the copper, aluminum, zinc and cobalt nitrates.

144.96 g of trihydrated cupric nitrate (0.6 g.at Cu), 116.41 g of hexahydrated cobalt nitrate (0.4 g.at Co), 450.15 g of nonahydrated aluminum nitrate (1.2 g.at Al), 267.72 g of hexahydrated zinc nitrate (0.9 g.at Zn) and 0.92 g of palladium nitrate (0.004 g.at Pd) are dissolved in 6 liters of bi-exchanged water so as to obtain a solution I containing 0.52 g.at of metals per liter.

Separately 427.18 g of disodic carbonate are dissolved in 7 liters of bi-exchanged water. The obtained solution (solution II) contains 1.15 g.at of sodium per liter.

Precipitation, thermal activation and shaping are the same as in example 1. The product obtained by precipitation was found homogeneous at the scale of 5 nanometers: the variation of the Cu/Co, Al/Co, Zn/Co and Pd/Co ratios is lower than 15% in proportion to the average value of each of them.

All the catalysts of examples 1 to 11 were tested in gaseous phase in a pilot plant operating continuously and with 20 cc of catalyst. The catalysts were previously reduced in situ by a hydrogen and nitrogen mixture of 6% hydrogen content, in successive heating steps between 160° C. and 240° C. and then with pure hydrogen in successive heating steps between 240° and 270° C., under atmospheric pressure.

The test conditions were as follows:
Temperature: 270° C. to 320° C.
Pressure: 6 megapascals (MPa)
Hourly volume velocity: 3000 $h^{-1}$
$H_2/2CO+3CO_2$ ratio: 1

The catalytic performances of these catalysts are reported in Table III hereinafter and defined as follows:
the activity is expressed in terms of weight productivity (r), as the number of kilograms of product per kilogram of catalyst per hour.
the selectivity by weight to higher alcohols $S(C_2{}^+OH)$, is expressed by the weight ratio:

$100 \times$ weight of $C_2{}^+OH$ alcohols/total weight of the formed alcohols the selectivity of the CO and $CO_2$ conversion to alcohol ($S_A$), expressed in carbon atom %, in proportion to all the carbon oxides, is defined as:

$$S_A = 100 \times \frac{N_C}{g.\ mol.\ (CO + CO_2)_{input} - g.\ mol.\ (CO + CO_2)_{output}}$$

wherein $N_C = C_1OH + 2\ C_2OH + 3\ C_3OH + \ldots nC_nOH$ = number of gram molecules of $(CO+CO_2)$ converted to alcohols.

the reaction by-products are mainly $C_2{}^+$ hydrocarbons and certain oxygenated compounds (aldehydes, esters, ketones) present as traces. The purity (p) of the alcohol in the liquid is expressed by the ratio of the total weight of alcohols in the liquid phase to the total weight of the organic liquid phase containing, in addition to the alcohols, other by-products of the reaction such as hydrocarbons and other oxygenated products: aldehydes, esters, ketones.

The purity is thus expressed as:

$$P = \frac{ROH\ weight}{\Sigma(ROH + hydrocarbons + oxygenated\ products)} \times 100$$

wherein ROH represents all the alcohols contained in the liquid phase.

At the start the methanation is expressed by the selectivity to methane, defined as:

$$S_{CH_4} = \frac{100 \times n\ (CH_4\ formed\ moles)}{m\ (disappeared\ CO + CO_2\ moles)}$$

after 17 hours of reaction.

The composition of the catalysts is given in Table II where the percent of each metal is expressed by weight in proportion to the total metals weight of the catalyst. The performances after 100 hours and 1000 hours of run are given in Table III.

TABLE II

| Example | Catalyst | Formula | Na % | Cu % | Co % | Al % | Zn % | B % or C % or M % | Cu/Al | Co/Al | Zn/Al | Na/Al |
|---|---|---|---|---|---|---|---|---|---|---|---|---|
| 1 | A | $Cu_{0.6}Co_{0.4}Al_{1.2}Zn_{0.9}Na_{0.00234}O_{3.9}$ | 0.035 | 24.93 | 15.41 | 21.17 | 38.47 | — | 0.5 | 0.33 | 0.75 | $1.95\ 10^{-3}$ |
| 2 | B | $Cu_{0.9}Co_{0.4}Al_{1.2}Zn_{0.6}Na_{0.00232}O_{3.9}$ | 0.035 | 37.52 | 15.46 | 21.24 | 25.72 | — | 0.75 | 0.33 | 0.5 | $1.93\ 10^{-3}$ |
| 3 | C* | $Cu_{1.05}Co_{0.4}Al_{1.2}Zn_{0.45}Na_{0.00231}O_{3.9}$ | 0.035 | 43.87 | 15.5 | 21.29 | 19.34 | — | 0.875 | 0.33 | 0.375 | $1.92\ 10^{-3}$ |
| 4 | D* | $Cu_{0.6}Co_{0.4}Al_{1.2}Zn_{0.9}Na_{0.116}O_{3.96}$ | 1.72 | 24.52 | 15.16 | 20.82 | 37.83 | — | 0.5 | 0.33 | 0.75 | $9.66\ 10^{-2}$ |
| 5 | E* | $Cu_{0.6}Co_{0.4}Al_{1.2}Zn_{0.9}Na_{0.362}O_{4.08}$ | 5.17 | 23.64 | 14.61 | 20.10 | 36.48 | — | 0.5 | 0.33 | 0.75 | $3.02\ 10^{-1}$ |
| 6 | F | $Cu_{0.6}Co_{0.4}Al_{1.2}Zn_{0.9}Na_{6.64\ 10^{-4}}O_{3.9}$ | 0.01 | 24.93 | 15.41 | 21.17 | 38.47 | — | 0.5 | 0.33 | 0.75 | $5.53\ 10^{-4}$ |
| 7 | G | $Cu_{0.6}Co_{0.4}Al_{1.2}Zn_{0.9}O_{3.9}$ | — | 24.93 | 15.42 | 21.18 | 38.47 | — | 0.5 | 0.33 | 0.75 | 0 |
| 8 | H | $Cu_{0.6}Co_{0.4}Al_{1.0}Mn_{0.2}Zn_{0.9}Na_{0.0017}O_{3.9}$ | 0.025 | 24.05 | 14.87 | 17.02 | 37.11 | 6.93 | 0.6 | 0.4 | 0.9 | $1.7\ 10^{-3}$ |
| 9 | I | $Cu_{0.6}Co_{0.4}Al_{1.2}Zn_{0.8}Cd_{0.1}Na_{0.0013}O_{3.9}$ | 0.019 | 24.18 | 14.95 | 20.54 | 33.17 | 7.13 | 0.5 | 0.33 | 0.66 | $1.1\ 10^{-3}$ |
| 10 | K | $Cu_{0.65}Co_{0.4}Al_{0.9}Zn_1Na_{0.0011}O_{3.6}$ | 0.016 | 26.72 | 15.25 | 15.72 | 42.3 | — | 0.72 | 0.44 | 1.11 | $1.2\ 10^{-3}$ |
| 11 | M | $Cu_{0.6}Co_{0.4}Al_{1.2}Zn_{0.9}Pd_{0.004}Na_{0.00231}O_{3.9}$ | 0.035 | 24.85 | 15.37 | 21.11 | 38.36 | 0.28 | 0.5 | 0.33 | 0.75 | $1.95\ 10$ |

*Catalyst for comparison

The number of oxygen gram-atoms is given as indication, with respect to oxides.

% by weight in proportion to the total metals weight.

Atomic ratios

TABLE III

| Catalyst | Start $S(CH_4)\%$ | Performances at 100 h | | | | | | Performances at 1000 h | | | | |
|---|---|---|---|---|---|---|---|---|---|---|---|---|
| | | T °C. | P(MPa) | r | $S_A$ % | $S(C_2{}^+OH)\%$ | p | T °C. | P(MPa) | r | $S_A$ % | $S(C_2{}^+OH)\%$ | p |
| A | 19 | 290 | 6 | 0.09 | 72 | 35 | 99.3 | 305 | 6 | 0.09 | 75 | 33 | 99.2 |
| B | 25 | 295 | 6 | 0.09 | 68 | 30 | 99 | 310 | 6 | 0.085 | 66 | 28 | 99 |
| C* | 43 | 290 | 6 | 0.085 | 50 | 25 | 98.7 | 300 | 6 | 0.060 | 50 | 20 | 98.8 |
| D* | 30 | 290 | 6 | 0.065 | 61 | 45 | 96.8 | 310 | 6 | 0.070 | 62 | 35 | 97.2 |
| E* | 44 | 290 | 6 | 0.07 | 55 | 62 | 83.2 | 310 | 6 | 0.072 | 52 | 50 | 80.3 |

TABLE III-continued

| Cata-lyst | Start S(CH₄)% | Performances at 100 h | | | | | | Performances at 1000 h | | | | | |
|---|---|---|---|---|---|---|---|---|---|---|---|---|---|
| | | T °C. | P(MPa) | r | S$_A$ % | S(C₂⁺OH)% | p | T °C. | P(MPa) | r | S$_A$ % | S(C₂⁺OH)% | p |
| F | 15 | 290 | 6 | 0.09 | 75 | 33 | 99.8 | 295 | 6 | 0.09 | 76 | 33 | 99.7 |
| G | 20 | 295 | 6 | 0.09 | 74 | 33 | 99.8 | 300 | 6 | 0.085 | 74 | 30 | 99.8 |
| H | 27 | 295 | 6 | 0.095 | 65 | 39 | 99.1 | 310 | 6 | 0.09 | 69 | 36 | 99.3 |
| I | 18 | 290 | 6 | 0.085 | 74 | 32 | 99.6 | 305 | 6 | 0.085 | 75 | 29 | 99.7 |
| K | 22 | 290 | 6 | 0.09 | 72 | 34 | 99.4 | 300 | 6 | 0.085 | 70 | 33 | 99.2 |
| M | 17 | 295 | 6 | 0.09 | 76 | 32 | 99.7 | 310 | 6 | 0.09 | 77 | 30 | 99.7 |

*Catalyst for Comparison r, S$_A$, S(C₂⁺OH) and p: definitions see example 11

What is claimed as the invention is:

1. A process for manufacturing primary alcohols by reaction of carbon oxides with hydrogen in the presence of a catalyst comprising, by weight:

| | |
|---|---|
| 15–45% | copper |
| 9–20% | cobalt |
| 7–25% | aluminum |
| 15–50% | zinc |
| 0–0.05% | alkali metal and/or alkaline earth metal, | wherein the atomic ratios of the metals are:

| | |
|---|---|
| 0.5:1 to 1.5:1 | for Zn/Al, |
| 0.25:1 to 0.55:1 | for Co/Al, and |
| 0.4:1 to 2:1 | for Cu/Al, | any variation in atomic ratios of Al/Co, Cu/Co and Zn/Co being lower than 10% with respect to the average value of said ratios on the 5 nm scale.

2. A process according to claim 1, wherein alkali metals and/or alkaline earth metals are present and the catalyst contains not more than 0.05% by weight of alkali metals or alkaline earth metals.

3. A process according to claim 1, wherein up to 50% of the aluminum atoms are substituted by at least one metal selected from the group consisting of chromium, titanium and manganese in manganic state, and/or up to 50% of the zinc atoms are substituted by at least one metal selected from the group consisting of cadmium and manganese in manganous state, the atomic ratio Zn/Al ranging from 0.5:1 to 1.5:1.

4. A process according to claim 1, wherein the atomic ratio alkali and/or alkaline-earth metal/Al is from 0:1 to 0.02:1.

5. A process according to claim 1, wherein the catalyst is produced by dissolving in water, in the presence of at least one organic complexing agent, at least one soluble compound of each of copper, cobalt, aluminum and zinc, said organic complexing agent being selected from the group formed of acid-alcohols, polyacids, amino-acids and amino-alcohols and used in a proportion of 0.5–2 gram equivalents of acid COO⁻ or of amine —NH₂ per gram equivalent of metals M$^{n+}$/n, the resultant solution being evaporated under reduced pressure and then dehydrated so as to obtain a vitreous compound, said compound being thermally activated in the presence of an inert gas containing from 0.1 to 100% of hydrogen, or in the presence of an inert gas containing from 0 to 50% of oxygen, in the range of about 300°–600° C., and finally shaped.

6. A process according to claim 1, wherein the catalyst is obtained after drying and thermal activation, at about 300°–600° C. and for at least 0.5 hour, of a hydrated precursor, said catalyst precursor, at least partly crystallized, being obtained by coprecipitation of a solution of soluble salts of Cu, Co, Al and Zn metals, whose total metals concentration is 0.1–1 gram-atoms of metals per liter, with a solution of sodium and/or potassium and/or ammonium carbonate and/or bi-carbonate and/or hydroxide whose total concentration of alkali metals and/or NH₄⁺ is from 0.1 to 2 gram-atoms per liter, the coprecipitation reaction being conducted at a pH of 7±1 pH unit at a temperature of at least 50° C. and with a residence time in the reaction medium from 3 to 180 minutes, the hydrated coprecipitate being then washed to reduce its alkali metals content (expressed as weight of alkali metal in proportion to the metals) to less than about 0.05% by weight, then matured between 50° and 250° C. in the presence of liquid water, for 15 minutes to 5 hours, the coprecipitate being dried, then thermally activated in the presence of an inert gas containing 0.1 to 100% of hydrogen or in the presence of an inert gas containing 0 to 50% of oxygen, between about 300° C. and about 600° C. and finally shaped.

7. A process according to claim 6, wherein the hydrated precipitate is washed to reduce its alkali metals content (expressed as weight of alkali metals in proportion to the total metals weight) to less than 0.05% by weight.

8. A process according to claim 1, wherein the reaction of carbon oxides with hydrogen is conducted at 200°–400° C. under 2–25 MPa with a molar ratio H₂/2CO+3CO₂ of 0.4:1 to 10:1.

9. A process according to claim 1, wherein the reaction of carbon oxides with hydrogen is performed in the presence of a liquid phase comprising one or more hydrocarbons having at least 5 carbon atoms per molecule.

10. A process according to claim 1, wherein the catalyst further contains 0.01 to 1% by weight of at least one noble metal from group VIII of the periodic classification.

11. A process according to claim 3, characterized in that said catalyst further contains from 0.01% to 1% by weight of at least one noble metal from group VIII.

12. A process according to claim 1, said catalyst having a specific surface from 20 to 300 m²×g⁻¹.

13. A process according to claim 12, characterized in that up to 50% of the zinc atoms have been substituted with at least one metal selected from the group consisting of cadmium and manganese in the manganous state and/or up to 50% of the aluminum atoms have been substituted with at least one metal, selected from the group consisting of chromium, titanium and manganese in the manganic state, the Zn/Al atomic ratio being from 0.5:1 to 1.5:1.

14. A process according to claim 13, wherein the reaction of carbon oxides with hydrogen is conducted at 200°–400° C. under 2–25 MPa with a molar ratio H₂/2CO+3CO₂ of 0.4:1 to 10:1.

15. A process according to claim 10, wherein said noble metal is rhodium, palladium or platinum.

16. A process according to claim 13, wherein the reaction of carbon oxides with hydrogen is performed in the presence of a liquid phase comprising one or more hydrocarbons having at least 5 carbon atoms per molecule.

17. A process according to claim 1, wherein said primary alcohols contain up to 1% b.w. based on the total weight of organic compounds present of esters, liquid hydrocarbon impurities, ketones and aldehydes.

18. A process according to claim 1, wherein the catalyst is free of alkali and/or alkaline earth metals.

19. A process according to claim 6, wherein the hydrated coprecipitate is matured in the presence of its mother waters.

20. A process according to claim 19, wherein the washed hydrated coprecipitate is matured in the presence of the washing waters.

21. A process according to claim 5, wherein up to 50% of the aluminum atoms are substituted by at least one metal selected from the group consisting of chromium, titanium and manganese in manganic state, or up to 50% of the zinc atoms are substituted by at least one metal selected from the group consisting of cadmium and manganese in manganous state, or both aluminum and zinc are so substituted, the atomic ratio Zn/Al ranging from 0.5:1 to 1.5:1.

22. A process according to claim 6, wherein up to 50% of the aluminum atoms are substituted by at least one metal selected from the group consisting of chromium, titanium and manganese in manganic state, or up to 50% of the zinc atoms are substituted by at least one metal selected from the group consisting of cadmium and manganese in manganous state, or both aluminum and zinc are so substituted, the atomic ratio Zn/Al ranging from 0.5:1 to 1.5:1.

23. In a process for manufacturing primary alcohols by reaction of carbon oxides in the presence of a catalyst, in which reaction transient methanation occurs, the improvement wherein the catalyst consists essentially of:

| | |
|---|---|
| 15–45% | copper |
| 9–20% | cobalt |
| 7–25% | aluminum |
| 15–50% | zinc |
| 0–0.05% | alkali metal or alkaline earth metal, | wherein the atomic ratios of the metals are:

| | |
|---|---|
| 0.5:1 to 1.5:1 | for Zn/Al, |
| 0.25:1 to 0.55:1 | for Co/Al, and |
| 0.4:1 to 2:1 | for Cu/Al, | any variation in atomic ratios of Al/Co, Cu/Co and Zn/Co being lower than 10% with respect to the average value of said ratios on the 5 nm scale.

* * * * *